US011613679B2

(12) United States Patent
Hwang et al.

(10) Patent No.: US 11,613,679 B2
(45) Date of Patent: Mar. 28, 2023

(54) ADHESIVE COMPOSITION, ADHESIVE COMPRISING SAME, AND MANUFACTURING METHOD THEREFOR (71) Applicants: KOLON INDUSTRIES, INC., Seoul (KR); KOREA ADVANCED INSTITUTE OF SCIENCE AND TECHNOLOGY, Daejeon (KR)

(72) Inventors: Hong Gu Hwang, Seoul (KR); Ick Kyung Sung, Seoul (KR); Du Hwan Kim, Seoul (KR); Jung Seok Hahn, Seoul (KR); Haeshin Lee, Daejeon (KR); Dai Heon Lee, Daejeon (KR)

(*) Notice: Subject to any disclaimer, the term of this patent is extended or adjusted under 35 U.S.C. 154(b) by 431 days.

(21) Appl. No.: 16/638,401

(22) PCT Filed: Aug. 22, 2018

(86) PCT No.: PCT/KR2018/009654
§ 371 (c)(1),
(2) Date: Feb. 11, 2020

(87) PCT Pub. No.: WO2019/039858
PCT Pub. Date: Feb. 28, 2019

(65) Prior Publication Data
US 2020/0362208 A1    Nov. 19, 2020

(30) Foreign Application Priority Data

Aug. 23, 2017 (KR) .................. 10-2017-0106364
Aug. 21, 2018 (KR) .................. 10-2018-0097589

(51) Int. Cl.
*C09J 129/04* (2006.01)
*A61K 47/32* (2006.01)
(Continued)

(52) U.S. Cl.
CPC ............. *C09J 129/04* (2013.01); *A61K 47/22* (2013.01); *A61K 47/32* (2013.01); *C09J 11/08* (2013.01)

(58) Field of Classification Search
None
See application file for complete search history.

(56) References Cited

U.S. PATENT DOCUMENTS 4,564,649 A * 1/1986 Hume, III ............ C09J 197/005
                                                        524/72
6,146,497 A   11/2000 Nguyen
(Continued)

FOREIGN PATENT DOCUMENTS

CN       103459542 A    12/2013
CN       105950071 A    9/2016
(Continued)

OTHER PUBLICATIONS

Office Action issued by Japan Patent Office dated Feb. 24, 2021.
(Continued)

*Primary Examiner* — Melissa S Mercier
(74) *Attorney, Agent, or Firm* — Harvest IP Law, LLP (57) ABSTRACT The present invention relates to an adhesive composition comprising a polyvinyl alcohol and a water-soluble polyphenol compound, to an adhesive comprising the same, and to a manufacturing method therefor and, more specifically, to an adhesive composition, which has little toxicity, can adhere even without a curing process unlike a conventional adhesive, enables the manufacturing of a gel by hydrogen binding characteristics between the polyvinyl alcohol compound and the water-soluble polyphenol compound, and retains adhesive properties in water.

20 Claims, 2 Drawing Sheets (51) Int. Cl.
*A61K 47/22* (2006.01)
*C09J 11/08* (2006.01)

(56) References Cited

U.S. PATENT DOCUMENTS

| | | |
|---|---|---|
| 2008/0200593 A1 | 8/2008 | Yue et al. |
| 2010/0258033 A1* | 10/2010 | Yang ............... C09J 189/00 |
| | | 106/144.71 |
| 2012/0064061 A1 | 3/2012 | Lee et al. |
| 2012/0156164 A1 | 6/2012 | Park et al. |
| 2013/0045393 A1 | 2/2013 | Brouns et al. |
| 2013/0202885 A1 | 8/2013 | Dodge et al. |
| 2017/0198142 A1 | 7/2017 | Hampson et al. |

FOREIGN PATENT DOCUMENTS

| | | |
|---|---|---|
| CN | 106364202 A | 2/2017 |
| CN | 106668931 A | 5/2017 |
| EP | 0320227 A2 | 6/1989 |
| GB | 488033 A | 6/1938 |
| JP | 61-062573 A | 3/1986 |
| JP | H04266901 A | 9/1992 |
| JP | 2001303459 A | 10/2001 |
| JP | 2013538280 A | 10/2013 |
| KR | 2001-0034195 A | 4/2001 |
| KR | 10-2006-0111381 A | 10/2006 |
| KR | 10-2011-0025530 A | 3/2011 |
| KR | 10-2012-0028175 A | 3/2012 |
| KR | 10-2017-0052567 A | 5/2015 |
| KR | 10-2016-0146825 A | 12/2016 |
| WO | 97/30114 A1 | 8/1997 |
| WO | 2005/056708 A2 | 6/2005 |
| WO | 2015/115453 A1 | 8/2015 |
| WO | 2016133483 A1 | 8/2016 |

OTHER PUBLICATIONS

Sample, C., "Hydrogen-Bonded Layer-by-Layer Assembly of Poly(Vinyl Alcohol) and Tannic Acid", Jun. 2014, Massachusetts Institute of Technology, 30 pages total.
Guan, et al., "Bio-inspired natural polyphenol cross-linking poly-(vinyl alcohol) films with strong integrated strength and toughness", 2016, Royal Society of Chemistry, vol. 6, 7 pages total.
Waite, J., "Nature's underwater adhesive specialist", 1987, International Journal of Adhesion and Adhesives, vol. 7, Issue 1, 6 pages total.
Zheng, et al., "Imparting Biomimetic Ion-Gating Recognition Properties to Electrodes with a Hydrogen-Bonding Structured Core-Shell Nanoparticle Network", 2000, Analytical Chemistry, vol. 72, Issue 10, 10 pages total.
Shin, et al., "DNA/Tannic Acid Hybrid Gel Exhibiting Biodegradability, Extensibility, Tissue Adhesiveness, and Hemostatic Ability", 2015, Advanced Functional Materials, vol. 25, 9 pages total.
Search Report dated Dec. 5, 2018, issued by the International searching Authority in counterpart International Patent Application No. PCT/KR2018/009654 (PCT/ISA/210).
Written Opinion dated Dec. 5, 2018, issued by the International searching Authority in counterpart International Patent Application No. PCT/KR2018/009654 (PCT/ISA/237).
Office Action issued by Chinese Patent Office dated Feb. 1, 2021.
Office Action issued by European Patent Office dated Feb. 23, 2021.

* cited by examiner

ADHESIVE COMPOSITION, ADHESIVE COMPRISING SAME, AND MANUFACTURING METHOD THEREFOR

TECHNICAL FIELD

The present invention relates to an adhesive composition, an adhesive comprising the same, and a preparation method thereof.

BACKGROUND ART

Adhesives are materials used to attach an object to the surface of another object. According to Internal Organization for Standardization (ISO), it is defined that 'adhesion means a state in which two surfaces are integrated by chemical and/or physical force, and adhesive is a material by which integration of two or more objects is allowed.'

Adhesives have been used widely in various fields, including daily life and industrial work due to their handiness. Such adhesives may be classified into inorganic adhesives and organic adhesives depending on their main ingredients. Organic adhesives may be further classified into synthetic organic adhesives and natural organic adhesives. Particularly, synthetic organic adhesives may be further classified into resin-based adhesives including thermosetting resins or thermoplastic resins, rubber-based adhesives, and mixed adhesives including phenolic adhesives and epoxy adhesives. However, in the case of synthetic organic adhesives, emission of harmful substances has become a serious problem recently. Such problems are caused by the use of volatile organic solvents and volatilization of unreacted monomers.

As such, various adhesives have been developed, but there are many difficulties in developing a composition that can be adhered in water, and in general. In the case of general underwater adhesives, they are often toxic. Therefore, there is a need to develop an adhesive composition that does not lose adhesive properties in water using harmless raw materials.

[Patent Document] Korean Laid-open Patent Publication No. 10-2012-0028175 (2012 Mar. 22), Adhesive composition comprising tannin, polyethylene glycol, and water, low carbon alcohol or the mixture thereof.

DISCLOSURE

Technical Problem

Accordingly, the inventors of the present invention have conducted many studies to develop an adhesive that is non-toxic, is not harmful to the human body, has moisture resistance and requires no heating upon curing, and as a result, have completed the present invention by confirming that the adhesive mixed with a polyvinyl alcohol and a polyphenol compound is hardly soluble in water and can be adhered in an underwater environment or an environment out of water without a curing process.

Therefore, it is an object of the present invention to provide an adhesive composition comprising a polyvinyl alcohol compound, a water-soluble polyphenol compound and water.

It is another object of the present invention to provide an industrial adhesive, a medical adhesive, an adhesive for underwater use, a sealant for underwater use, an adhesive patty, an adhesive tape, a moist wound healing dressing, a medical anti-adhesive agent or a controlled drug delivery adhesive comprising the composition described above.

Technical Solution

In order to achieve the above objects, the present invention provides an adhesive composition comprising a polyvinyl alcohol compound, a water-soluble polyphenol compound and water.

At this time, the polyvinyl alcohol compound may be in the form of a random copolymer.

At this time, the polyvinyl alcohol compound may be represented by the following Formula 1.

[Formula 1]

wherein n and m are the composition ratios of the monomers of the polyvinyl alcohol compound, n is 0.7 or more and 1.0 or less, m is 0 or more and 0.3 or less, and n+m=1.

At this time, the polyvinyl alcohol compound may comprise a functional group selected from the group consisting of hydroxyl group (OH), amine group (NH2), succinimidyl succinate, succinic acid, thiol group (SH), acrylate, epoxide group, maleimide, nitrophenyl carbonate, pyridyl disulfide, tosylate group, azide, phosphoric acid group, oligoamine group ([—CH2-CH2-NH-]n), catechol and catechol amine.

The water-soluble polyphenol compound may be at least one selected from the group consisting of hydroxybenzoic acid-based compound, hydroxycinnamic acid-based compound, flavonoid-based compound, lignan-based compound, stilbene-based compound, caffeic acid, chlorogenic acid, anthocyan, pyrogallol, ellagic acid, gallic acid, catechin, hydrolyzable tannin, condensed tannin and theaflavin gallate.

At this time, the hydrolyzable tannin may be at least one selected from the group consisting of tannic acid, gallotannins and ellagitannins.

At this time, the polyvinyl alcohol compound and the water-soluble polyphenol compound may be hydrogen-bonded to each other.

At this time, the composition may have a tensile adhesion strength in water of 10 kPa or more.

At this time, the content of the polyvinyl alcohol compound may be 5 to 60% by weight based on the total weight of the composition.

At this time, the content of the water-soluble polyphenol compound may be 20 to 70% by weight based on the total weight of the composition.

At this time, the content of water may be 10 to 60% by weight based on the total weight of the composition.

At this time, the composition may further comprise at least one selected from the group consisting of alcohols and organic solvents.

At this time, the composition may have a ratio of tensile adhesive strength after 10 times of attachment and detachment relative to the initial (once) attachment and detachment in water (tensile adhesive strength after 10 times of attachment and detachment/initial tensile adhesive strength) of 0.7 to 2.0, preferably 0.8 to 1.2.

At this time, the composition may have a ratio of the tensile adhesive strength out of the water and the tensile adhesive strength in the water (tensile adhesive strength in water/tensile adhesive strength out of water) of 0.7 to 1.3, preferably 0.8 to 1.2.

At this time, the composition may be used in an industrial adhesive, medical adhesive, an adhesive for underwater use, a sealant for underwater use, an adhesive patty, an adhesive tape, a moist wound healing dressing, and a medical anti-adhesive agent.

In addition, the present invention provides a controlled drug delivery adhesive comprising the composition.

At this time, the controlled drug delivery adhesive may be at least one selected from the group consisting of a sparingly soluble drug, a therapeutic peptide, a protein and an antibody.

In addition, the present invention provides a method for preparing an adhesive composition comprising the steps of (a) mixing a polyvinyl alcohol compound, a water-soluble polyphenol compound, and water; and (b) obtaining an adhesive composition mixed and formed in step (a).

In addition, the present invention provides a method for preparing an adhesive composition comprising the steps of (a) dissolving the polyvinyl alcohol compound in water; (b) dissolving the water-soluble polyphenol compound in water; (c) mixing the respective dissolved substances obtained in steps (a) and (b) to form an adhesive composition; and (d) obtaining the adhesive composition formed in step (c).

At this time, any one solvent of alcohols and organic solvents may be added to the water.

Advantageous Effects

The present invention relates to an adhesive composition comprising a polyvinyl alcohol compound and a water-soluble polyphenol compound, which has little toxicity, can adhere even without a curing process unlike a conventional adhesive, enables the preparation of a gel by hydrogen binding characteristics between the polyvinyl alcohol compound and the water-soluble polyphenol compound, and retains the adhesive property in water.

The adhesive composition can be applied to various fields such as a medical adhesive, an adhesive patch, an adhesive tape. a moist wound healing dressing, a drug delivery adhesive or a medical anti-adhesive agent.

BEST MODE

In the present invention, an adhesive composition comprising a polyvinyl alcohol compound, a water-soluble polyphenol compound and water is presented, which has little toxicity, can adhere even without a curing process unlike a conventional adhesive, enables the manufacturing of a gel by hydrogen binding characteristics between the polyvinyl alcohol compound and the water-soluble polyphenol compound, and retains the adhesive property in water.

Hereinafter, the present invention will be described in more detail.

Adhesive Composition

The adhesive composition referred to herein comprises a polyvinyl alcohol compound, a water-soluble polyphenol compound, and water. In the case of a general underwater adhesive, it is often toxic. However, the present invention provides an adhesive composition exhibiting water resistance in water using a harmless raw material.

The adhesive composition of the present invention comprises a polyvinyl alcohol. The polyvinyl alcohol compound (poly(vinyl alcohol), PVA) was first synthesized by Herrmann and Haehnel in 1924 during the saponification of polyvinyl acetate (poly (vinyl acetate), PVAc) and began to be commercialized as a resin for vinylon fiber in Japan after World War II.

In general, since vinyl alcohol, which is a monomer, is unstable, the polyvinyl alcohol (PVA) cannot be obtained by polymerization of vinyl alcohol, and is mainly prepared by producing PVAc through emulsion polymerization from vinyl acetate and then hydrolyzing it with alkali or acid.

Depending on the degree of hydrolysis of PVAc, the constituents of the resulting PVA are determined (n and m in Formula 1 described below), which is generally referred to as a degree of saponification or a degree of hydrolysis. For example, if n=0.88 and m=0.12 in Formula 1, the degree of hydrolysis of the PVA of Formula 1 is said to be 88%.

The PVA prepared from saponification of PVAc is a white powdery polymer that is easy to form a film and a fiber, and has high surface activity, high mechanical strength and adhesive strength, and excellent solubility and chemical reactivity. In addition, the PVA is biodegradable, water soluble, and degraded by bacteria found in the soil, and thus is in the spotlight as a material for sensitive use in the protection of the environment. The PVA has a very wide range of applications, and thus is widely used in applications ranging from household products to highly functional industrial materials.

The PVA was used in a cardboard, a veneer board, an office adhesive, a binder for ferrite or ceramic, a solid parasiticide, a fermented soil, a fiber sizing agent, a thickening agent for color printing, a laundry starch, a coating or reinforcing agent for paper, an emulsifying agent for emulsion polymerization or suspension polymerization, a stabilizer, a sponge and the like, and until recently, has been used in an asbestos fiber, high performance fiber for replacing concrete rebar, an environmental-friendly water-soluble fiber, and various optical films and separators including a polarizing film depending on molecular weight and stereoregularity, and also is used as state-of-the-art materials such as a hydrogel for replacing human organs, drug delivery systems, bioreactor, biosensor, and embolic materials for treating cancer diseases and angioplasty.

The polyvinyl alcohol compound of the present invention may be in the form of a random copolymer, and specifically, the polyvinyl alcohol compound of Formula 1 may be used.

[Formula 1]

wherein n and m are the composition ratio of the polyvinyl alcohol compound, n is 0.7 or more and 1.0 or less, m is 0 or more and 0.3 or less, and n+m=1.

In Formula 1, when n is less than 0.7 or m is more than 0.3, the content of the PVA is lowered, so that the water-soluble property (solubility) is lowered, thereby making it difficult to prepare a solution of the polyvinyl alcohol compound.

In addition, the polyvinyl alcohol compound may comprise a functional group selected from the group consisting of hydroxyl group (OH), amine group (NH2), succinimidyl succinate, succinic acid, thiol group (SH), acrylate, epoxide group, maleimide, nitrophenyl carbonate, pyridyl disulfide (orthopyridyl disulfide), tosylate group, azide, phosphoric acid group, oligoamine group ([—CH2-CH2-NH-]n), catechol and catechol amine. For example, the epoxy functional group may be present in combination with each monomer of Chemical Formula 1, and it may react with the hydroxyl group (—OH) of the polyphenol compound to form a chemical bond.

The polyvinyl alcohol compound of the present invention can be applied as a polyvinyl alcohol compound of various molecular weights, depending on the field to which the adhesive composition is applied, and thus is not specified in terms of the molecular weight of the polyvinyl alcohol compound, but preferably may have a weight average molecular weight (Mw) of 5,000 to 2,000,000. As the weight average molecular weight of the polyvinyl alcohol compound is reduced, the flexibility of the prepared adhesive composition is increased and the adhesive property (tackiness, stickiness) of the surface is increased. As the weight average molecular weight of the polyvinyl alcohol compound is increased, the flexibility is decreased and the adhesive property of the surface is decreased, but it appears characteristics that the internal cohesion of the composition is increased.

The polyvinyl alcohol compound may be contained in an amount of 5 to 60% by weight, more preferably in an amount of 15 to 40% by weight, based on the total weight of the adhesive composition prepared in the present invention. If the content of the polyvinyl alcohol compound is lower than 5% by weight, there is a problem that the flexibility of the adhesive composition is lowered. If the content of the polyvinyl alcohol compound exceeds 60% by weight, there is a problem that the water resistance is reduced and thus it is easily dissolved in water.

The adhesive composition of the present invention comprises a water-soluble polyphenol compound.

In relation to the water-soluble polyphenol compound, a substance in which one of the hydrogens in the benzene ring (C6H6) is substituted with a hydroxyl group (—OH) is called phenol, and substances having two or more hydroxyl groups are referred to collectively as a water-soluble polyphenol, or a polyhydric phenol. Compounds with this structure exist in nature a lot. Catechins contained in green tea, chlorogenic acid contained in coffee, and red or purple anthocyanin pigments contained in strawberries, eggplants, grapes, black soybeans, and adzuki beans are all polyphenol compounds. In addition, the polyphenol compounds can be found in many varieties, such as vegetables, fruits, cacao and red wine.

The polyphenols have the effect of preventing oxidation, that is, antioxidant activity. The reason why polyphenols are attracting attention recently is that their function is expected to contribute to maintaining health and preventing disease by acting as an antioxidant in vivo. In addition, the polyphenols prevent cholesterol from being absorbed into the digestive tract, thereby acting to lower the level of the cholesterol in the blood.

The water-soluble polyphenol compound of the present invention may be at least one selected from the group consisting of hydroxybenzoic acid-based compound, hydroxycinnamic acid-based compound, flavonoid-based compound, lignan-based compound, stilbene-based compound, caffeic acid, chlorogenic acid, anthocyan, pyrogallol, ellagic acid, gallic acid, catechin, hydrolyzable tannin, condensed tannin and theaflavin-3-gallate, and specifically, the hydrolyzable tannin may be one or more selected from the group consisting of tannic acid, gallotannins, and ellagitannins, but is not necessarily limited thereto.

In addition, the water-soluble polyphenol compound of the present invention may be specifically selected from the group consisting of tannic acid of Formula 2, gallic acid of Formula 3, ellagic acid of Formula 4, catechin of Formula 5, and polymers thereof. The weight average molecular weight of the water-soluble polyphenol compound is not particularly limited, but may be preferably 100 to 10,000.

[Formula 2]

[Formula 3]

MW: 170.12

[Formula 4]

MW: 302.197

[Formula 5]

MW: 290.26

The water-soluble polyphenol compound may be contained in an amount of 20 to 70% by weight, more preferably in an amount of 30 to 55% by weight based on the total weight of the adhesive composition prepared in the present invention. If the content of the water-soluble polyphenol compound is lower than 20% by weight, there is a problem in the water-resistant adhesion of the adhesive composition. If the content of the water-soluble polyphenol compound exceeds 70% by weight, there is a problem that the flexibility is reduced.

In the adhesive composition of the present invention, the polyvinyl alcohol compound and the water-soluble polyphenol compound may be hydrogen-bonded to each other, as shown in Scheme 1 below.

[Scheme 1]

Scheme 1 shows a hydrogen bond between tannic acid, which is a water-soluble polyphenol compound, and the polyvinyl alcohol compound. The adhesive composition of the present invention can be prepared in the form of a gel, since a hydrogen bond is formed between the polyvinyl alcohol compound and the water-soluble polyphenol compound, as in Formula 6. The adhesive composition of the present invention improves the solubility of PVA in water, thereby enabling the characteristics of the adhesive composition that can be used in an underwater environment Therefore, the adhesive composition of the present invention may have excellent underwater adhesive force, and specifically may have a tensile adhesive strength of 10 kPa or more in water, preferably a tensile adhesive strength of 30 kPa to 300 kPa in water, and more preferably a tensile adhesive strength of 50 kPa to 100 kPa.

In particular, if the content ratio (based on solids) of the water-soluble polyphenol compound/polyvinyl alcohol compound is 0.5 or more, the tensile adhesive strength in water may be 30 kPa to 300 kPa, and more preferably the tensile adhesive strength in water may be 50 kPa to 100 kPa.

If the adhesive strength in water is less than 30 kPa, the adhesive force is too low to be suitable for application as an underwater adhesive. If the adhesive force is 300 kPa or more, it may be difficult to achieve the composition claimed in the present invention. However, since the upper limit of adhesive force can be overcome depending on the applied pressure, the time required, the attachment time, water or the type of solvent in the attachment process, and the temperature in the attachment process, the upper limit of tensile adhesive strength in water obtained from this is not necessarily limited.

In addition, it can be seen that since the adhesive composition of the present invention may have a ratio of the tensile adhesive strength out of the water and the tensile adhesive strength in the water (tensile adhesive strength in water/tensile adhesive strength out of water) of 0.7 to 1.3, preferably 0.8 to 1.2, the adhesive force in water does not drop compared to the adhesive force out of water.

In addition, the composition may have a ratio of tensile adhesive strength after 10 times of attachment and detachment relative to the initial (one time) attachment and detachment in water (tensile adhesive strength after 10 times of attachment and detachment/initial tensile adhesive strength) of 0.7 to 2.0, preferably 0.8 to 1.2, and can maintain the adhesive force even if used for a long time in water.

The water contained in the adhesive composition of the present invention may be contained as the remaining amount, except for the polyvinyl alcohol compound and the water-soluble polyphenol compound, and preferably, 10 to 60 wt. % based on the total weight of the composition.

The adhesive composition of the present invention may further contain at least one selected from the group consisting of alcohols and organic solvents.

The alcohol used in the present invention is not particularly limited, but may be lower alcohol, such as methanol, ethanol, normal propanol, isopropanol, butanol, amyl alcohol, normal amyl alcohol, isoamyl alcohol, normal hexyl alcohol, preferably ethanol.

There is no particular limitation to the organic solvent used in the present invention.

In addition, the adhesive composition of the present invention may contain an additive for improving cohesion, in order to improve interface failure or cohesive failure characteristics by which the adhesive itself is destroyed. The additive may be an additive capable of hydrogen-bonding, chelate-bonding, covalent-bonding by hydrophobic interaction, and ionic-bonding with the polyvinyl alcohol compound or the water-soluble polyphenol compound, and specifically may be used at least one selected from the group consisting of inorganic particles, metal particles, DNA, metal oxides or metal ions, BSA and protein.

In addition, the adhesive composition of the present invention may further contain an additive for improving its physical properties and the like, and may further contain thickeners for improving the viscosity, plasticizers for decreasing the viscosity, dyes and pigments for the appearance of color, ultraviolet absorbers and ultraviolet stabilizers for the stability of light, antistatic agents for preventing static electricity.

The adhesive composition of the present invention may be used in an industrial adhesive, a medical adhesive, an adhesive for underwater use, a sealant for underwater use, an adhesive patty, an adhesive tape, a moist wound healing dressing, and a medical anti-adhesive agent.

In addition, the adhesive composition of the present invention can be used for the adhesion of adherends made from wood or wood materials.

As used herein, the term 'adhesion' refers to a conventional meaning, which means to solidify at an initial time and then become inelastic with time, and also means that when detached again, it is difficult to reattach. However, as used herein, the term "adhesion" is meant to comprise "stickiness". The term "stickiness" refers to something that can be easily adhered by pressure and re-adhered several times after detachment, which is in the form of a state in which a viscoelastic characteristic is maintained. The adhesive composition of the present invention has a property as a sticking agent.

The adhesive of the present invention is nontoxic. Therefore, the adhesive composition of the present invention can be used as a medical adhesive, can be directly in contact with the skin, and is characterized in that it is not toxic and dangerous even when the adhesive is used in vivo and flows into body fluids and blood and thus is directly involved in the living body.

Therefore, the adhesive composition of the present invention can be used in a medical adhesive, a moist wound healing dressing, an anti-adhesive agent and the like.

The medical adhesive refers to an adhesive that can be applied to a wide range of fields from the packaging of medical devices in a broad sense to the surgical sticking, adhesion and hemostasis, and is biocompatible and thus can be used directly on the skin and generally has no toxicity and risk completely even when directly involved in a living body so that it can be used in vivo. To be used as a medical adhesive, the medical adhesive should have biodegradability, water resistance, sterility, non-toxic property and hemostatic effects in addition to biocompatibility, and should not interfere with the healing of the living body. The adhesive of the present invention has a use as a medical adhesive, and the use comprises a use as a sticking agent. More specifically, the adhesive of the present invention can be used in vivo as a surgical adhesive hemostatic agent and a medical adhesive for suture after colon incision.

The anti-adhesive agent refers to a material that maintains as a physical barrier for a period of time at a site where adhesion is expected, and thus serves to prevent adhesion formation between adjacent tissues. Therefore, the anti-adhesive agent should be decomposed or absorbed into the body after a certain period of time and thus should not remain as foreign substances. The adhesive composition of the present invention may be contained in the preparation of an anti-adhesive agent that prevents the adhesion that may be induced after a surgical operation.

The moist wound healing dressing has sufficient antimicrobial activity to effectively treat or prevent serious infections by various pathogenic bacteria that cause deterioration of the wound site, delay the treatment, and cause complications, and it also provides a wet environment by the absorption of exudate, thereby rapidly increasing the growth rate of epithelial cells for skin regeneration, and is to alleviate the pain, shorten the treatment period, minimize the scar after treatment, and the like. Therefore, for use in the moist wound healing dressing, it must be non-toxic. Since the adhesive composition of the present invention is non-toxic, it can be used as a moist wound healing dressing.

In addition, the adhesive of the present invention is characterized by having a water resistance that can be used even in an aqueous environment. As used herein, the term 'water resistance' refers to a property capable of maintaining the adhesive force even in an environment where water is present, for example, in an environment where moisture is present. In order to have water resistance, it must not dissolve well in a material with high humidity or an aqueous solution containing water and must be able to stably maintain adhesion even in the presence of a fluid flow. Since the adhesive of the present invention has a property of being sparingly soluble in water, the adhesive agent of the present invention can be utilized as an adhesive for underwater use, a sealant for underwater use, and the like which has a moisture resistance.

In addition, the adhesive composition of the present invention may be used as a controlled drug delivery adhesive, and thus may contain a therapeutic drug for this purpose, and for example, may contain a sparingly soluble drug, therapeutic peptide, protein and antibody that can be delivered by a controlled drug delivery adhesive. Without being limited to these, examples of the sparingly soluble substance comprise paclitaxel and doxorubicin having a low molecular weight and the like, examples of therapeutic peptide comprise somatostatin, calicitonin, vasopressions, platelet coagulation inhibition peptides (platelet aggregate inhibitors), gornadotropin-releasing hormone and the like, examples of the protein and the antibody comprise an interleukin family, erythropoietin (EPO), granulocyte colony-stimulating factor (G-CSF), human growth hormone and the like. In the present invention, the type of drug is not particularly limited.

In addition, the present invention relates to a method for preparing an adhesive composition the steps of (a) mixing a polyvinyl alcohol compound, a water-soluble polyphenol compound, and water; and (b) obtaining an adhesive composition mixed and formed in step (a). The preparation method of the adhesive composition of the present invention is described as follows for each step.

Step (a) is a step of mixing a polyvinyl alcohol compound, a water-soluble polyphenol compound, and water.

The adhesive composition of the present invention is prepared by mixing the polyvinyl alcohol compound, the water-soluble polyphenol compound and water. In addition to water, a solvent of any one of alcohols and organic solvents may be further added. In mixing the materials, the order of mixing is not limited to that as described above.

Step (b) is a step of obtaining an adhesive composition mixed and formed in step (a).

The mixture of step (a) does not cause an additional reaction during mixing, and it is possible to obtain an adhesive composition without a separate process. When mixing the two mixtures, the gelation process proceeds rapidly, and a liquid consisting of water, alcohol, organic solvent, unreacted polyvinyl alcohol compound and unreacted polyphenol compound and an adhesive substance in gel state are separated.

In addition, the present invention relates to a method for preparing an adhesive composition the steps of (a) a step of dissolving the polyvinyl alcohol compound in water; (b) a step of dissolving the water-soluble polyphenol compound in water; (c) a step of mixing the respective dissolved substances obtained in steps (a) and (b) to form an adhesive composition; and (d) a step of obtaining the adhesive composition formed in step (c). The preparation method is described as follows for each step.

Step (a) is a step of dissolving the polyvinyl alcohol compound in water, and step (b) is a step of dissolving the water-soluble polyphenol compound in water. In steps (a) and (b), any one of alcohols and organic solvents in addition to water may be further added. These are the processes of dissolving the water-soluble polyphenol compound and the polyvinyl alcohol compound, which are the compositions of the present invention discussed above, in water, respectively to make them easy to mix, and the processes are independent steps. In addition, a buffer for pH adjustment may be used when preparing dissolved substance.

Step (c) is a step of mixing the respective dissolved substances obtained in steps (a) and (b) to form an adhesive composition.

This step is a step to form an adhesive composition by mixing the dissolved substances of the polyvinyl alcohol compound and the water-soluble polyphenol compound of the present invention, and the mixing order is not limited to the described order, and the mixing volume ratio is the same as discussed above.

Step (d) is a step of obtaining the adhesive composition of step (c).

The mixture of the present invention does not cause an additional reaction during mixing, it is possible to obtain the adhesive composition from the mixture without a separate process, and the brown material corresponds to the adhesive composition of the present invention.

Hereinafter, the preparation method of the adhesive composition of the present invention through the examples of the present invention will be described in more detail. It is to be understood that the present invention is not limited to these examples.

EXAMPLE

Preparation of Adhesive Composition

Examples 1~5

To 80 g of water, 20 g of polyvinyl alcohol compound of formula a (PVA, weight average molecular weight of 13,000~23,000, degree of hydrolysis of 87~89%) was added and stirred at 85° C. for 5 hours in an oven to prepare 20 wt. % of aqueous PVA solution. 40 wt. % of an aqueous PVA solution was prepared in the same manner as described above.

To 50 g of water, 50 g of tannic acid (Formula b) was added, and stirred at room temperature for 24 hours to prepare 50 wt. % of aqueous TA solution. 10, 20, 30, and 40 wt. % of aqueous TA solution were prepared, respectively, in the same manner as described above.

The aqueous solution of the polyvinyl alcohol and the aqueous solution of tannic acid were quantified in the same amount (weight ratio of 1:1) as shown in Table 1 and Table 2, and stirred for 10 minutes using a spatula to prepare an adhesive composition.

TABLE 1

| Item | Example 1 | Example 2 | Example 3 | Example 4 | Example 5 |
|---|---|---|---|---|---|
| Aqueous PVA solution | 40 wt.% | 40 wt.% | 40 wt.% | 40 wt.% | 40 wt.% |
| Aqueous TA solution | 5 wt.% | 10 wt.% | 20 wt.% | 30 wt.% | 40 wt.% |
| Content ratio (TA solids/PVA solids) | 0.125 | 0.25 | 0.5 | 0.75 | 1.0 |

TABLE 2

| Item | Example 6 | Example 7 | Example 8 | Example 9 | Example 10 |
|---|---|---|---|---|---|
| Aqueous PVA solution | 20 wt.% | 20 wt.% | 20 wt.% | 20 wt.% | 20 wt.% |
| Aqueous TA solution | 5 wt. % | 10 wt.% | 20 wt.% | 30 wt. % | 40 wt.% |
| TA/PVA content ratio (TA solids/PVA solids) | 0.25 | 0.5 | 1.0 | 1.5 | 2.0 |

Thereafter, these were treated for 10 minutes at 10 kRPM using a centrifuge to obtain an adhesive composition that sank to the bottom.

[Formula a]

-continued

[Formula b]

Comparative Example 1

An adhesive composition was prepared by mixing 38 μl of linear poly ethylene glycol (PEG, weight average molecular weight of 2 kDa) at a concentration of 1 g/mL and 162 μl of tannic acid (Formula b) at a concentration of 1 g/mL, in accordance with the method described in Example 1 of Korean Patent No. 10-1307367.

EXPERIMENTAL EXAMPLES

Experimental Example 1: Measurement of the Adhesive Force in Water

Figure 1:
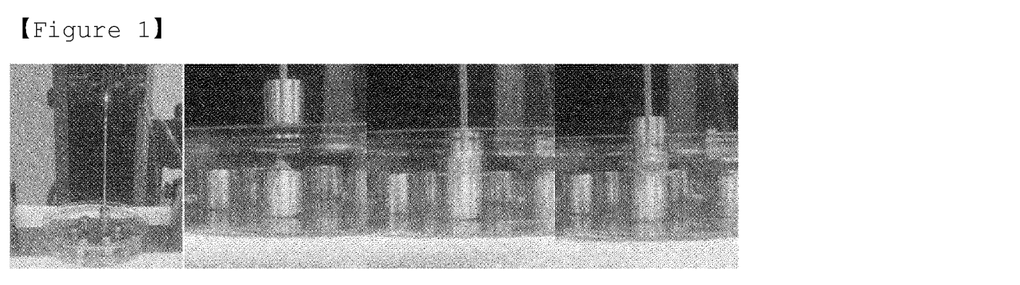
FIG. 1 is a photograph showing a method of measuring the adhesive force of the adhesive composition of the present invention.

In order to measure the adhesive force in water of the adhesive compositions prepared in Examples 1 to 10 and Comparative Example 1, the device was designed as shown in FIG. 1 to measure the tensile adhesive strength in water.

A cylindrical specimen having a diameter of 10 mm was made of SUS, attached to a water bath, and filled with water, and then 40 mg of an adhesive composition was coated on the cylindrical specimen in water. Using a cylindrical specimen having a diameter of 10 mm made of SUS material, the adhesive composition was pressed for 30 seconds with a force of 5 N, and then detached at a rate of 1 mm/min to measure its tensile adhesive strength in water, and the process thereof was shown in FIG. 1.

Figure 2:
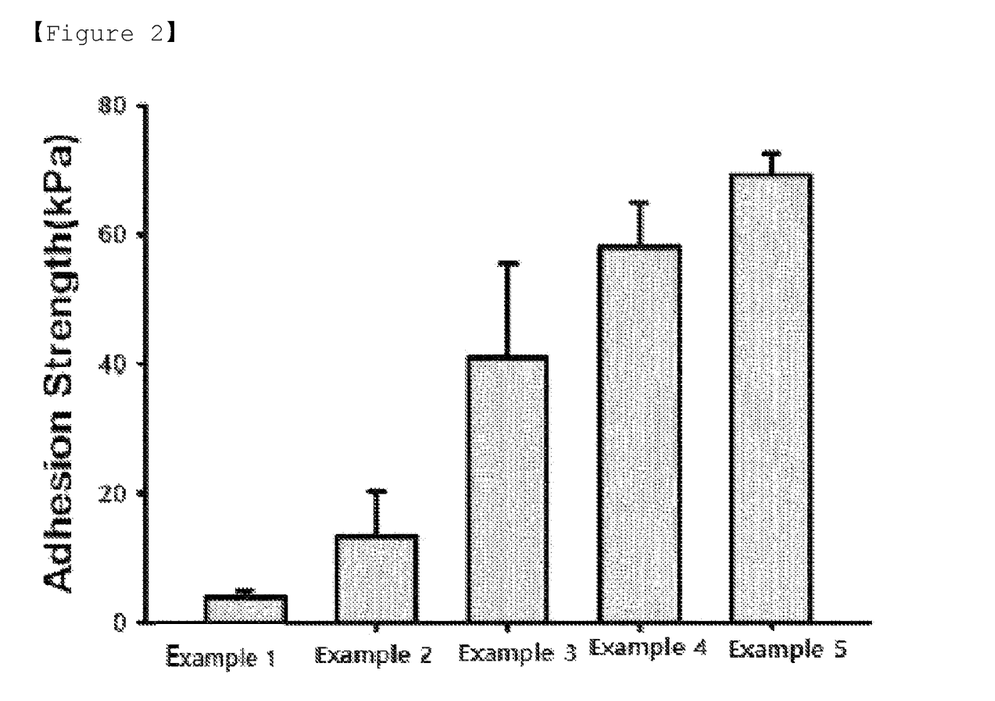
FIG. 2 is a graph of the results obtained by measuring tensile adhesive strength in water of the adhesive compositions prepared in Examples 1 to 5.
Figure 3:
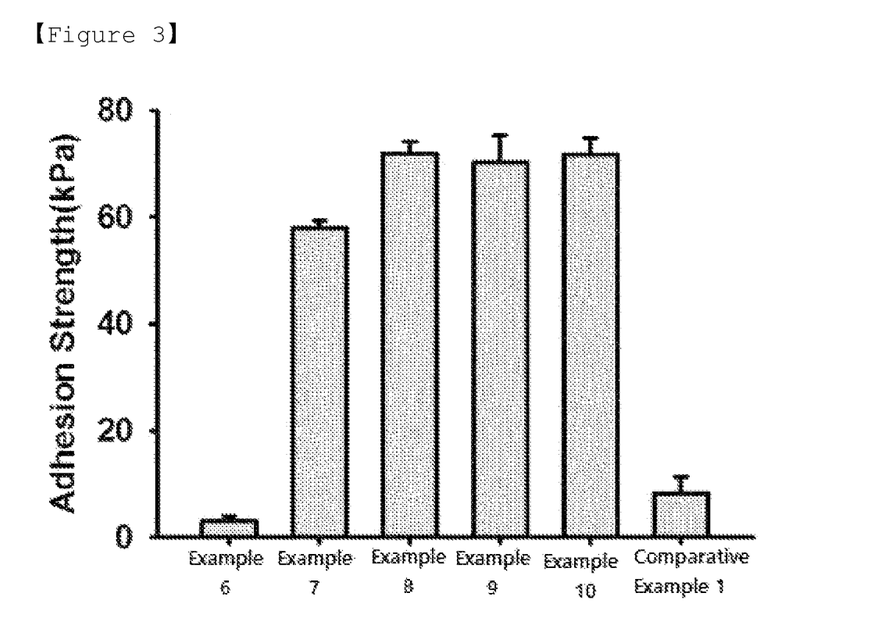
FIG. 3 is a graph of the results obtained by measuring tensile adhesive strength in water of the adhesive compositions prepared in Examples 6 to 10.

In addition, the tensile adhesive strength in water of the adhesive compositions prepared in Examples 1 to 10 were shown in FIGS. 2 and 3. As a result of the analysis of the tensile adhesive strength in water of Examples 1 to 10, it was confirmed that the tensile adhesive strength in water at 30 kPa or more was expressed at a TA/PVA content ratio (TA solids/PVA solids) of 0.5 or more that was employed to prepare the adhesive composition, and it was confirmed that when the TA/PVA content ratio (TA solids/PVA solids) was 1.0 or more, the adhesive force showed the maximum value. It was confirmed that the adhesive composition thus prepared showed higher adhesive property than Comparative Example 1. Therefore, in the preparation of the adhesive composition, the adhesive composition produced at a TA/PVA content ratio (TA solids/PVA solids) of 0.5 or more employed in the initial blending is preferable as the adhesive, and more preferably, it is determined to be 1.0 or more. The adhesive composition produced at a TA/PVA content ratio (TA solids/PVA solids) of 0.5 or more and 4.0 or less employed in the initial blending is preferable as the adhesive, and more preferably, it is determined to be 2.0 or more.

In the case of two materials after blending at a TA/PVA content ratio of 2.0 or 4.0 or more employed in the initial blending, TA does not all participate in the composition formed from hydrogen bonding or interaction, and exists as supernatant. There is a disadvantage that the yield of the resulting composition is lowered due to this phenomenon. Of course, since the TA solution can be reused by a method of reprocessing a solution existing as a supernatant, the TA/PVA content ratio (TA solids/PVA solids) employed in the initial blending is not necessarily upper-limited in the present invention.

Experimental Example 2: Measurement of Adhesive Force in Water Storage

After coating and storing in water for a certain time, the degree of change in adhesive force over time was confirmed. The tensile adhesive strength was measured for the adhesive composition prepared in Example 8 in the same manner as in Experimental Example 1, while varying the storage time after coating in water.

Figure 4:
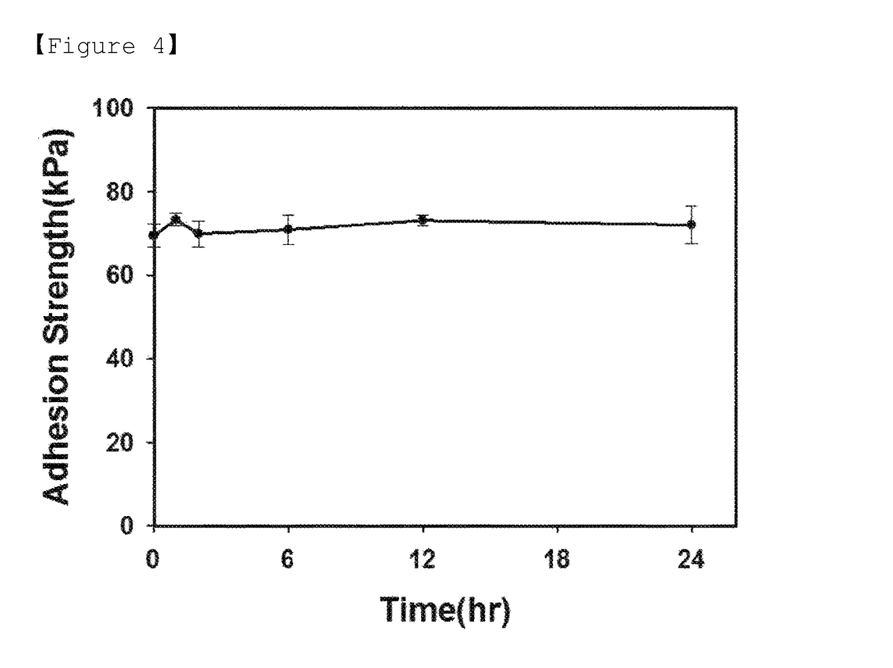
FIG. 4 is a graph showing the tensile adhesive strength measured while varying the storage time after coating the adhesive composition prepared in Example 8 in water.

As shown in FIG. 4, it was found that after coating in water, the ratio of the initial tensile adhesive strength in water within 1 hour and the tensile adhesive strength in water after 24 hours (tensile adhesive strength in water after 24 hours/initial tensile adhesive strength in water within 1 hour) was 0.8 to 1.2, and thus the width of change of the adhesive force with time was very low.

Experimental Example 3: Measurement of Adhesive Force According to Attachment and Detachment in Water The tensile adhesive strength according to the number of attachment and detachment in water was measured for the adhesive composition prepared in Example 3, and the results are shown in Table 3.

As shown in Table 3, it was confirmed that even if the attachment and detachment are carried out ten times in water, the adhesive force was not reduced, it was confirmed that the width of change in the ratio of tensile adhesive strength after initial (one time) and ten times attachment and detachment is 0.8 to 1.2 or less.

Therefore, it was confirmed that the adhesive composition of the present invention can be attached and detached in plural in water.

TABLE 3

| Number of attachments and detachments | Tensile adhesive strength (kPa) | Tensil adhesive strength after relevant number of times/initial tensile adhesive strength |
|---|---|---|
| 1 (initial adhesion) | 65.2 | 0.96 |
| 2 | 62.3 | 1.03 |
| 3 | 67.4 | 0.93 |
| 4 | 60.5 | 0.98 |
| 5 | 63.6 | 1.05 |
| 6 | 68.2 | 1.10 |
| 7 | 71.9 | 1.01 |
| 8 | 65.7 | 1.07 |
| 9 | 69.8 | 1.11 |
| 10 | 72.4 | 0.96 |

Experimental Example 4: Measurement of Tensile Adhesive Strength in and Out of Water The tensile adhesive strength in water and out of water was measured using the adhesive composition prepared in Example 3, and was measured while varying its applied pressure to 5N and 10N. The results are shown in Table 4.

TABLE 4

| Item | Tensile adhesive strength in water (kPa) | Tensile adhesive strength out of water (kPa) | Ration of tensile adhesive strength in water/tensile adhesive strength out of water |
|---|---|---|---|
| Applied pressure_5N | 65.2 | 67.2 | 0.97 |
| Applied pressure_10N | 69.0 | 66.8 | 1.03 |

As shown in Table 4, the adhesive composition of the present invention exhibited excellent tensile adhesive strength in water and out of water, and it was confirmed that the ratio of the tensile adhesive strength out of water and in water is maintained at a constant ratio (0.8 to 1.2).

The invention claimed is:

1. An adhesive composition comprising a polyvinyl alcohol compound, a water-soluble polyphenol compound, and water,
    wherein the content of the polyvinyl alcohol compound is 15 to 40 wt. % based on the total weight of the composition,
    wherein the content of the water-soluble polyphenol compound is 20 to 70 wt. % based on the total weight of the composition,
    wherein the weight average molecular weight of the polyvinyl alcohol compound is 13,000 to 23,000.

2. The adhesive composition according to claim 1, wherein the polyvinyl alcohol compound is represented by the following Formula 1,

[Formula 1]

wherein n and m are the composition ratios of the monomers of the polyvinyl alcohol compound, n is 0.7 or more and 1.0 or less, m is 0 or more and 0.3 or less, and n+m=1.

3. The adhesive composition according to claim 1, wherein the polyvinyl alcohol compound comprises a functional group selected from the group consisting of hydroxyl group (OH), amine group (NH2), succinimidyl succinate, succinic acid, thiol group (SH), acrylate, epoxide group, maleimide, nitrophenyl carbonate, pyridyl disulfide, tosylate group, azide, phosphoric acid group, oligoamine group ([—CH2-CH2-NH—]n), catechol and catechol amine.

4. The adhesive composition according to claim 1, wherein the content ratio (based on solids) of the water-soluble polyphenol compound/polyvinyl alcohol compound is 0.5 or more.

5. The adhesive composition according to claim 1, wherein the water-soluble polyphenol compound is at least one selected from the group consisting of hydroxybenzoic acid-based compound, hydroxycinnamic acid-based compound, flavonoid-based compound, stilbene-based compound, caffeic acid, chlorogenic acid, anthocyan, pyrogallol, gallic acid, ellagic acid, catechin, hydrolyzable tannin, condensed tannin and theaflavin-3-gallate.

6. The adhesive composition according to claim 5, wherein the hydrolyzable tannin is at least one selected from the group consisting of tannic acid, gallotannins and ellagitannins.

7. The adhesive composition according to claim 1, wherein the polyvinyl alcohol compound and the water-soluble polyphenol compound are hydrogen bonded to each other.

8. The adhesive composition according to claim 1, wherein the composition has a tensile adhesive strength of 30 kPa or more in water.

9. The adhesive composition according to claim 1, wherein the content of the polyvinyl alcohol compound is 5 to 60 wt. % based on the total weight of the composition.

10. The adhesive composition according to claim 1, wherein the content of the water-soluble polyphenol compound is 20 to 70 wt. % based on the total weight of the composition.

11. The adhesive composition according to claim 1, wherein the water content is 10 to 60% by weight based on the total weight of the composition.

12. The adhesive composition according to claim 1, wherein the composition further comprises at least one selected from the group consisting of alcohols and organic solvents.

13. The adhesive composition according to claim 1, wherein the composition has a ratio of tensile adhesive strength in and out of water (tensile adhesive strength in water/tensile adhesive strength out of water) of 0.8 to 1.2.

14. The adhesive composition according to claim 1, wherein the composition has a ratio of tensile adhesive strength after 10 times of attachment and detachment relative to the initial (once) attachment and detachment in water (tensile adhesive strength after 10 times of attachment and detachment/initial tensile adhesive strength) of 0.8 to 1.2.

15. The adhesive composition according to claim 1, wherein the composition has a ratio of the initial tensile adhesive strength in water within 1 hour and the tensile adhesive strength in water after 24 hours after coating in water (tensile adhesive strength in water after 24 hours/initial tensile adhesive strength in water within 1 hour) of 0.8 to 1.2.

16. The adhesive composition according to claim 1, wherein the composition is used in an industrial adhesive, a medical adhesive, an adhesive for underwater use, a sealant for underwater use, an adhesive patty, an adhesive tape, a moist wound healing dressing, or a medical anti-adhesive agent.

17. The adhesive composition according to claim 1, wherein the composition is used for the adhesion of adherends made from wood or wood materials.

18. A controlled drug delivery adhesive comprising the composition of claim 1.

19. A method for preparing an adhesive composition comprising the steps of:
   (a) dissolving the polyvinyl alcohol compound in water;
   (b) dissolving the water-soluble polyphenol compound in water;
   (c) mixing the respective dissolved substances obtained in steps (a) and (b) to form an adhesive composition; and
   (d) obtaining the adhesive composition formed in step (c).

20. An adhesion method for underwater use, using the adhesive composition according to claim 1.

* * * * *